(12) United States Patent
Woo et al.

(10) Patent No.: US 10,076,254 B2
(45) Date of Patent: Sep. 18, 2018

(54) OPTICAL COMMUNICATION WITH OPTICAL SENSORS

(71) Applicant: Microsoft Technology Licensing, LLC, Redmond, WA (US)

(72) Inventors: Kevin Woo, Bellevue, WA (US); Ceasar Barcenas de Leon, Redmond, WA (US); Vinod L. Hingorani, Redmond, WA (US); Erik Holverson, Bellevue, WA (US)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 497 days.

(21) Appl. No.: 14/572,587

(22) Filed: Dec. 16, 2014

(65) Prior Publication Data

US 2016/0166153 A1  Jun. 16, 2016

(51) Int. Cl.
*A61B 5/1455* (2006.01)
*A61B 5/024* (2006.01)
*A61B 5/00* (2006.01)
*H04B 10/114* (2013.01)

(52) U.S. Cl.
CPC ...... *A61B 5/02427* (2013.01); *A61B 5/02438* (2013.01); *A61B 5/14552* (2013.01); *A61B 5/681* (2013.01); *H04B 10/1143* (2013.01); *A61B 2560/0214* (2013.01); (Continued)

(58) Field of Classification Search
CPC .............. A61B 5/1455; A61B 5/02416; A61B 5/14552; A61B 5/7207; A61B 5/4818; A61B 5/0205; A61B 5/14532; A61B 5/72; A61B 5/02427; A61B 5/681; (Continued)

(56) References Cited

U.S. PATENT DOCUMENTS 5,846,190 A * 12/1998 Woehrle ............ A61B 5/14551
                                          600/330
6,126,595 A * 10/2000 Amano ................... A61B 5/02
                                          600/300
7,810,504 B2    10/2010 Guzman
(Continued)

FOREIGN PATENT DOCUMENTS

WO    2011033628 A1    3/2011
WO    2014063160 A1    4/2014

OTHER PUBLICATIONS

Fingas, Jon, "TomTom's new GPS watches track your heart rate without a chest strap (update: US pricing)", http://www.engadget.com/2014/04/03/tomtom-cardio-gps-watches/, Apr. 3, 2014, 10 pages.
(Continued)

*Primary Examiner* — Eric Winakur
*Assistant Examiner* — Chu Chuan (JJ) Liu
(74) *Attorney, Agent, or Firm* — Alleman Hall Creasman & Tuttle LLP

(57) ABSTRACT

A wearable computing device includes an electro-optical sensor to translate received light into an electrical signal. During a first mode of operation of the wearable computing device, a physical parameter of a wearer of the wearable computing device is assessed from the electrical signal. During a second mode of operation of the wearable computing device, encoded communication data is extracted from the electrical signal.

20 Claims, 5 Drawing Sheets

(52) U.S. Cl.
CPC . *A61B 2560/0456* (2013.01); *A61B 2562/222* (2013.01); *A61B 2562/228* (2013.01)

(58) Field of Classification Search
CPC .......... A61B 5/6824; A61B 2560/0214; A61B 2560/0456; A61B 2562/222; A61B 2562/228; A61B 5/14551
See application file for complete search history.

(56) References Cited

U.S. PATENT DOCUMENTS

| | | | |
|---|---|---|---|
| 8,547,036 | B2 | 10/2013 | Tran |
| 8,579,827 | B1 | 11/2013 | Rulkov et al. |
| 8,779,349 | B2* | 7/2014 | West .................. A61B 5/14551 600/331 |
| 2003/0212316 | A1 | 11/2003 | Leiden et al. |
| 2011/0098583 | A1 | 4/2011 | Pandia et al. |
| 2012/0108928 | A1 | 5/2012 | Tverskoy |
| 2012/0293410 | A1 | 11/2012 | Bell |
| 2013/0064552 | A1 | 3/2013 | Fortune et al. |
| 2013/0183042 | A1 | 7/2013 | Knapp et al. |
| 2013/0195273 | A1 | 8/2013 | Lord |
| 2013/0274565 | A1 | 10/2013 | Langer et al. |
| 2013/0305053 | A1* | 11/2013 | Laffey .................. H04L 9/3247 713/176 |
| 2013/0338470 | A1* | 12/2013 | Ouwerkerk .......... A61B 5/0533 600/384 |
| 2014/0131549 | A1 | 5/2014 | Kaskoun et al. |
| 2014/0159912 | A1 | 6/2014 | Fraden |
| 2014/0213863 | A1* | 7/2014 | Loseu ................ A61B 5/02416 600/324 |
| 2014/0243612 | A1 | 8/2014 | Li et al. |
| 2014/0266787 | A1 | 9/2014 | Tran |
| 2014/0275871 | A1* | 9/2014 | Lamego ............... A61B 5/0022 600/316 |
| 2014/0275874 | A1* | 9/2014 | Haisley ................ H02J 7/0042 600/323 |
| 2014/0288390 | A1* | 9/2014 | Hong ................ A61B 5/02427 600/301 |

OTHER PUBLICATIONS

Goode, Lauren, "Samsung's New Gear Fit Needs to Work on the "Fit" Part", http://recode.net/2014/04/08/samsungs-new-gear-fit-needs-to-work-on-the-fit-part/, Apr. 8, 2014, 10 pages.

"Samsung Gear Fit, Gear 2 and Gear 2 Neo go on sale worldwide", NDTV Gadgets, http://gadgets.ndtv.com/others/news/samsung-gear-fit-gear-2-and-gear-2-neo-go-on-sale-worldwide-507220, Apr. 11, 2014, 3 pages.

Poeter, Damon, "Meet Simband, Samsung's Next-Gen Health Tracker", http://www.pcmag.com/article2/0,2817,2458663,00.asp, May 28, 2014, 5 pages.

Bursky, Dave, "Wireless Medical and Fitness System Design Guidelines Leverage Low-power Communications Protocols", Published on: Feb. 27, 2014 Available at: http://www.digikey.com/en/articles/techzone/2014/feb/wireless-medical-and-fitness-system-design-guidelines-leverage-low-power-communications-protocols.

ISA European Patent Office, International Search Report and Written Opinion Issued in Application No. PCT/US2015/065425, dated May 20, 2016, WIPO, 13 Pages.

IPEA European Patent Office, Second Written Opinion Issued in PCT Application No. PCT/US2015/065425, dated Oct. 24, 2016, WIPO, 6 Pages.

IPEA European Patent Office, International Preliminary Report on Patentability Issued in PCT Application No. PCT/US2015/065425, dated Mar. 10, 2017, WIPO, 9 Pages.

* cited by examiner

OPTICAL COMMUNICATION WITH OPTICAL SENSORS

BACKGROUND

Some wearable computing devices comprise external electrical connection interfaces, such as a port for interfacing with a cable. Such an interface port may be used to communicate with remote computing devices, and/or charge a battery of the wearable computing device.

SUMMARY

In one example, a wearable computing device includes an electro-optical sensor to translate received light into an electrical signal. During a first mode of operation of the wearable computing device, a physical parameter of a wearer of the wearable computing device may be assessed from the electrical signal. During a second mode of operation of the wearable computing device, communication data encoded in the electrical signal may be extracted.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

DETAILED DESCRIPTION

A computing device, such as a wearable computing device, may include one or more external electrical-connection interfaces. A charging and communication port for interfacing with a cable is an example of one such interface. Conventional ports may provide an ingress for water, sweat, moisture, and other foreign objects. Conventional ports also may act as a point of failure of a wearable computing device. Furthermore, conventional ports may take up valuable real-estate that limits a form factor of a wearable computing device. Further still, conventional ports may act as an irritant to a wearer that has a skin allergy to commonly employed metal coatings.

The present description relates to an approach for utilizing electro-optical sensors and/or optical emitters of a wearable computing device to provide optical transmission functionality that enables robust communications with a remote computing device. In one example, a wearable computing device may be operated in a sensing/emitting mode in which an electro-optical sensor is operated to assess a physical parameter of a wearer of the wearable computing device. Further, the wearable computing device may be operated in a communication mode in which the electro-optical sensor is operated to enable the exchange of communication data with a remote computing device. Such an approach may eliminate a need for a separate port or other external electrical-connection interface to enable communication functionality. Moreover, such an approach may provide faster transmission speeds and less complex communications relative to over-the-air wireless communications.

Figure 1A:
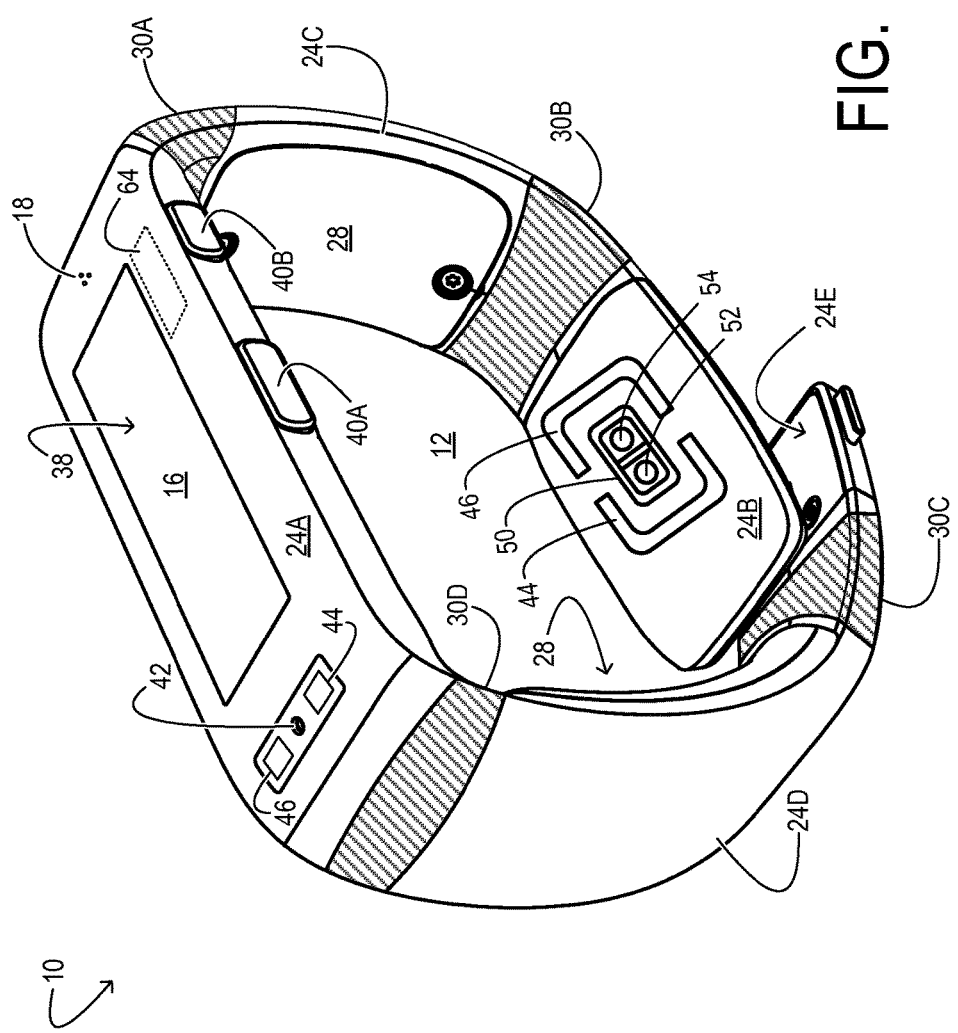
FIG. 1A shows aspects of an example wearable computing device.
Figure 1B:
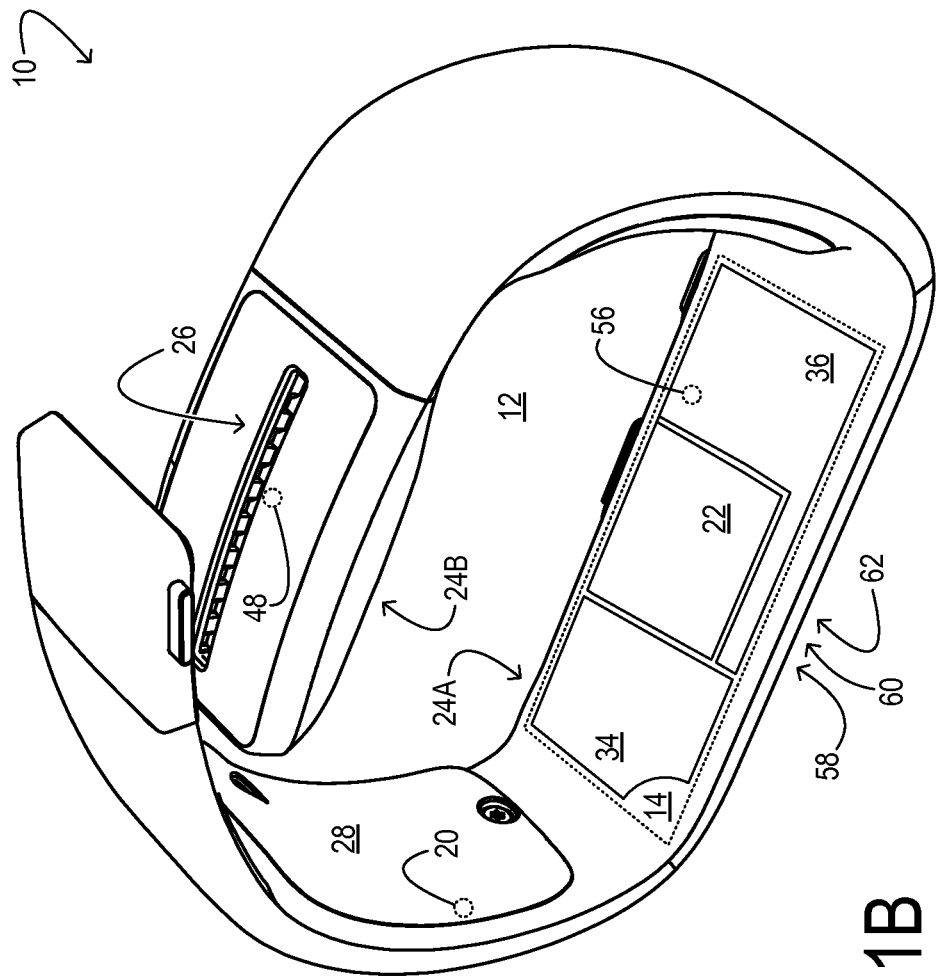
FIG. 1B shows additional aspects of the example wearable computing device.

FIGS. 1A and 1B show aspects of a wearable computing device 10 that includes features to facilitate efficient communication. The illustrated device 10 takes the form of a composite band 12. In one implementation, a closure mechanism enables facile attachment and separation of the ends of the composite band 12, so that the band 12 can be closed into a loop and worn on the wrist. In other implementations, the device 10 may be fabricated as a continuous loop resilient enough to be pulled over the hand and still conform to the wrist. Alternatively, the device 10 may have an open-bracelet form factor in which ends of the band are not fastened to one another. In still other implementations, wearable computing devices 10 of a more elongate band shape may be worn around the user's bicep, waist, chest, ankle, leg, head, or other body part. Accordingly, the wearable computing devices 10 here contemplated include eye glasses, a head band, an arm-band, an ankle band, a chest strap, or any other wearable form factor.

Furthermore, computing devices without wearable configurations may be employed in some implementations. For example, the herein described features may be employed in any suitable mobile computing device, such as a smartphone, tablet computer, laptop computer, or another suitable computing device.

As shown in the drawings, wearable computing device 10 may include various functional electronic components: a computing system 14, display 16, loudspeaker 18, haptic motor 20, communication suite 22, and various sensors. In the illustrated implementation, the functional electronic components are integrated into the several rigid segments of the band—viz., display-carrier module 24A, pillow 24B, energy-storage compartments 24C and 24D, and buckle 24E. This tactic protects the functional components from physical stress, from excess heat and humidity, and from exposure to water and substances found on the skin, such as sweat, lotions, salves, and the like. In the illustrated conformation of wearable computing device 10, one end of composite band 12 overlaps the other end. Buckle 24E is arranged at the overlapping end of the composite band 12, and receiving slot 26 is arranged at the overlapped end.

The functional electronic components of wearable computing device 10 draw power from one or more energy-storage electronic components 28. A battery—e.g., a lithium ion battery—is one type of energy-storage electronic component. Alternative examples include super- and ultra-capacitors. To provide adequate storage capacity with minimal rigid bulk, a plurality of discrete, separated energy-storage electronic components 28 may be used. These may be arranged in energy-storage compartments 24C and 24D, or in any of the rigid segments of composite band 12. In some implementations, energy-storage compartments 24C and 24D may be semi-rigid or flexible to accommodate flexible batteries. Electrical connections between the energy-storage electronic components 28 and the functional electronic components are routed through flexible segments 30 (e.g., 30A, 30B, 30C, 30D). In some implementations, the energy-storage electronic components 28 have a curved shape to fit comfortably around the wearer's wrist, or other body part.

In general, energy-storage electronic components 28 may be replaceable and/or rechargeable. In some examples, the energy-storage electronic components 28 may be recharged by wireless inductive or ambient-light charging. In other examples, external metal pads (e.g., of a galvanic skin response sensor) may act as Ohmic charging electrodes to receive an electrical charge for recharging the energy-storage electronic components 28. In still other examples, the wearable computing 10 device may include electro-mechanical componentry to recharge the energy-storage electronic components 28 from the user's adventitious or purposeful body motion.

In wearable computing device 10, computing system 14 is housed in display-carrier module 24A and situated below display 16. The computing system 14 is operatively coupled to display 16, loudspeaker 18, communication suite 22, and to the various sensors. The computing system 14 includes a data-storage machine 34 to hold data and instructions, and a logic machine 36 to execute the instructions.

Display 16 may be any suitable type of display, such as a thin, low-power light emitting diode (LED) array or a liquid-crystal display (LCD) array. Quantum-dot display technology may also be used. Suitable LED arrays include organic LED (OLED) or active matrix OLED arrays, among others. An LCD array may be actively backlit. However, some types of LCD arrays—e.g., a liquid crystal on silicon (LCOS) array—may be front-lit via ambient light. Although the drawings show a substantially flat display 16 surface, this aspect is by no means necessary, for curved display 16 surfaces may also be used. In some use scenarios, wearable computing device 10 may be worn with display 16 on the front of the wearer's wrist, like a conventional wristwatch.

In wearable computing device 10, touch-screen sensor 38 is coupled to display 16 and configured to receive touch input from the user. Accordingly, the display 16 may be a touch-sensor display in some implementations. In general, the touch-screen sensor 38 may be resistive, capacitive, or optically based. Push-button sensors (e.g., microswitches) may be used to detect the state of push buttons 40A and 40B, which may include rockers. Input from the pushbuttons 40A and 40B may be used to enact a home-key or on-off feature, control audio volume, microphone, or another suitable operation.

Wearable computing device 10 may also include motion sensing componentry, such as an accelerometer 58, gyroscope 60, and magnetometer 62. The accelerometer 58 and gyroscope 60 may furnish inertial data along three orthogonal axes as well as rotational data about the three axes, for a combined six degrees of freedom. This sensory data can be used to provide a pedometer/calorie-counting function, for example. Data from the accelerometer 58 and gyroscope 60 may be combined with geomagnetic data from the magnetometer 62 to further define the inertial and rotational data in terms of geographic orientation.

Wearable computing device 10 may also include a global positioning system (GPS) receiver 64 for determining the wearer's geographic location and/or velocity. In some configurations, the antenna of the GPS receiver 64 may be relatively flexible and extend into flexible segment 30A.

Wearable computing device 10 may also include microphone 42. The microphone 42 provides audio input to computing system 14 that may be used to measure an ambient sound level or receive voice commands from the wearer of the wearable computing device 10.

Wearable computing device 10 may include various temperature sensors including an ambient-temperature sensor 48 and a skin-temperature sensor 56. The ambient-temperature sensor 48 measures an ambient temperature of the surrounding environment. The skin-temperature sensor 56 provides a direct thermal conductive path to the skin. Output from ambient-temperature sensor 48 and skin-temperature sensor 56 may be applied differentially to estimate the heat flux from the wearer's body. This metric can be used to improve the accuracy of pedometer-based calorie counting, for example.

Wearable computing device 10 includes a pair of contact sensors—positive charging contact sensor or electrode 44 and negative contact sensor or electrode 46 arranged on pillow 24 of the band. Each contact sensor contacts the wearer's skin when wearable computing device 10 is worn and may also include plated contacts. The contact sensors may include independent or cooperating sensor elements, to provide a plurality of sensory functions. For example, the contact sensors may provide an electrical resistance and/or capacitance sensory function responsive to the electrical resistance and/or capacitance of the wearer's skin. To this end, the two contact sensors may be configured as a galvanic skin-response sensor, for example. Note that the pair of contact sensors may be omitted from the wearable computing device 10 in implementations where the wearable computing device 10 has no exposed metal contact pads or other external metal interfaces.

FIGS. 1A and 1B show various other electro-optical sensors, optical transducers, and optical emitters of wearable computing device 10 including an electro-optical sensor 50. Electro-optical sensor 50 may be arranged on an under-side of pillow 24B of the band, such that the electro-optical sensor 50 is facing a skin surface of the wearer of the wearable computing device 10. The electro-optical sensor 50 may include an optical emitter 52 and matched photodiode 54 or other light sensor.

The wearable computing device 10 may be configured operate in a sensing/emitting mode in which optical components may be used to assess different physical parameters of a wearer of the wearable computing device 10 or physical parameters of the surrounding environment. In one example, during operation in the sensing/emitting mode, the wearable computing device 10 may be configured to instruct the optical emitter 52 to emit a diagnostic reference light, and the photodiode 54 may translate received (e.g., reflected) light into an electrical signal. Further, during operation in the sensing/emitting mode, the wearable computing device 10 may be configured to recognize the electrical signal translated from the diagnostic reference light by the photodiode 54, and assess a physical parameter of the wearer of the wearable computing device 10 from the electrical signal.

In one example, the electro-optical sensor 50 includes an optical pulse rate sensor including an LED emitter to emit a green diagnostic reference light (e.g., ~525 nm) to illuminate pulsating blood flow through the capillaries of the skin, and thereby provides a measurement of the wearer's pulse rate. In some implementations, the optical pulse-rate sensor may also be configured to sense the wearer's blood pressure.

In another example, the electro-optical sensor 50 includes a pulse oximeter that monitors oxygen saturation by measuring a blood oxygen level of the wearer's blood. In one example, the optical emitter 52 of the pulse oximeter emits two wavelengths of diagnostic reference light (e.g., 660 nm and 940 nm) at a body part and light reflected back to the photodiode 54 is measured to determine changes in absorbance of light at each of the two wavelengths due to pulsing arterial blood flow. The blood oxygen level may be derived from such changes in absorbance.

In other examples, the electro-optical sensor 50 includes a sensor for measuring an environmental parameter of an environment in which the wearable computing device 10 is positioned. In one example, the electro-optical sensor 50 includes a proximity sensor that emits a diagnostic reference light and measures a reflected light to determine changes in the reflected light that indicate proximity to a foreign object. In another example, the electro-optical sensor 50 includes an ambient light sensor that measures an ambient light level. Any suitable environmental parameter may be measured by electro-optical sensor 50 without departing from the scope of the present disclosure. Note that an electro-optical sensor 50 may be configured to measure an environmental parameter when implemented in non-wearable computing device applications (e.g., a smartphone).

Furthermore, the wearable computing device 10 may be configured to operate in a communication mode in which the electro-optical sensor 50 may be used to send and/or receive communication data to/from a remote computing device (e.g., a host computing device that provides synchronization, processing, data storage, and other functionality to the wearable computing device 10). During the communication mode, the communication data may be encoded as light. In particular, the same optical emitter 52 that is used to measure physical parameters of the wearer may be used to flash pulses of light that encode communication data. These pulses may be received by another device. Similarly, the same photodiode 54 or other light sensor used to measure physical parameters of the wearer may be used to receive pulses of light that encode communication data. As such, the same light emitter and sensor may be used for both physical parameter assessment (e.g., heart rate measurement) and device-to-device communication.

In both the communication and sensing/emitting modes of operation, the same light sensor may be used to receive light and translate the received light into an electrical signal that can be further processed by the wearable computing device 10. In the sensing/emitting mode of operation, the received light is diagnostic reference light that comes from an optical emitter of the wearable computing device 10 (e.g., optical emitter 52). On the other hand, in the communication mode of operation, the received light is communication light that comes from a remote device.

During operation in the communication mode, the optical emitter 52 of the electro-optical sensor 50 need not emit a diagnostic reference light. Instead, the wearable computing device 10 may be configured to, during the communication mode, recognize an electrical signal translated from communication light received by the photodiode 54. For example, the communication light may be received from a communication cable. In downstream processing, the wearable computing device 10 may be configured to, during the communication mode, extract communication data encoded in the electrical signal derived from the communication light. Accordingly, communication data may be transferred from the remote computing device to the wearable computing device 10 with the photodiode 54 of the electro-optical sensor 50.

In some implementations, during the communication mode, the wearable computing device 10 may be configured to instruct the optical emitter 52 of the electro-optical sensor 50 to emit communication light encoding communication data. The communication light may have different properties than the diagnostic reference light (e.g., intensity, flash pattern and frequency). Accordingly, communication data may be transferred from the wearable computing device 10 to the remote computing device with the optical emitter 54 of the electro-optical sensor 50.

Because the electro-optical sensor 50 includes both the optical emitter 52 and the photodiode 54, communication data may transferred bi-directionally between the remote computing device and the wearable computing device 10 with the electro-optical sensor 50.

By leveraging operation of the electro-optical sensor 50 and other optical components to both assess a physical parameter and provide communication functionality, the functionality of two separate device systems may be combined in electro-optical sensor 50.

The wearable computing device 10 may sense a current mode of operation in any suitable fashion. As one example, the wearable computing device 10 will automatically switch to the communication mode of operation responsive to sensing connection of a communication cable. As another example, the wearable computing device 10 will automatically switch to the sensing/emitting mode responsive to sensing a galvanic skin response. In general, the wearable computing device 10 may automatically switch between the sensing/emitting mode and the communication mode responsive to any suitable event, trigger, or condition.

Communication suite 22 may include any appropriate communications I/O interface componentry. In FIGS. 1A and 1B, the communications suite 22 includes the electro-optical sensor 50 to provide bi-directional communication during operation in the communication mode. Note that although an electro-optical sensor 50 may replace functionality of an external electrical-connection interface, in some implementations, the wearable computing device 10 may still include one or more charging and/or communication ports or other external electrical-connection interfaces.

In one example, the above described optical communication approach may be employed when the wearable computing device 10 installs a corrupted version of software/firmware and has to recover to a previous version. In this case, universal receiver/transmitter (URT) and serial communication protocols that may be implemented for optical communication may be significantly less complex relative to protocol stacks of wireless and other communication protocols. Accordingly, in such scenarios, the wearable computing device 10 may be able to perform optical communication to recover functionality when other forms of communication (e.g., USB, Bluetooth, Wi-Fi) may be unavailable.

Wearable computing device 10 may include any suitable number and/or type of electro-optical sensors 50, optical transducers, and/or optical emitters to provide both sensing/emitting functionality and optical communication functionality with a remote computing device.

In some implementations, the communication suite 22 may include a USB port, which may be used for exchanging data between wearable computing device 10 and other computer systems, as well as providing recharge power. In some implementations, the communication suite 22 may include two-way Bluetooth (BT), Bluetooth Low Energy (BTLE), Wi-Fi, cellular, Ethernet, near-field communication, and/or other radios.

Wearable computing device 10 is merely one example of a computing device that uses existing optical components in a manner other than for assessing physical parameters in order to remove a need for additional electrical-communication interfaces. For example, other computing devices that do not have wearable functionality may employ optical components for dual sensing and communication purposes.

In one example, such an approach may be employed in a smartphone, a tablet computing device, a laptop computing device, or another mobile computing device.

Figure 2:
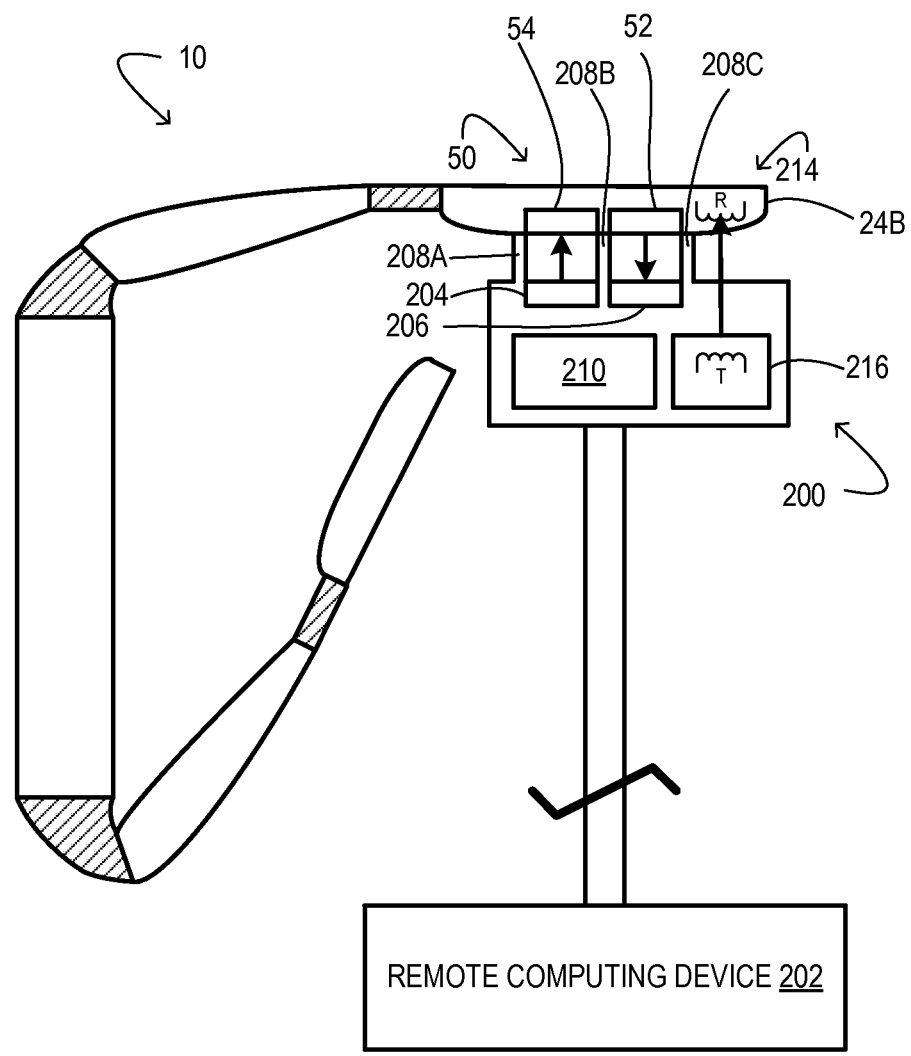
FIG. 2 shows an example implementation of a wearable computing device interfacing with a communication cable to enable optical communication with a remote computing device.

FIG. 2 shows an example implementation of the wearable computing device 10 interfacing with a communication cable 200 to enable optical communication with a remote computing device 202. The communication cable 200 may include an optical emitter 204 and an optical transducer 206 positioned to mirror the optical emitter 52 and the photodiode 54 of the electro-optical sensor 50 of the wearable computing device 10. In other words, the optical emitter 204 of the communication cable 200 may be configured to emit communication light encoded with communication data to the photodiode 54 to enable communication data to be sent from the remote computing device 202 to the wearable computing device 10. Correspondingly, the optical transducer 206 of the communication cable 200 may be configured to translate communication light emitted from the optical emitter 52 of the electro-optical sensor 50 to enable communication data to be sent from the wearable computing device 10 to the remote computing device 202.

An alignment mechanism 208 (e.g., 208A, 208B, 208C) may be configured to align the optical emitter 52 with the optical transducer 206 and the photodiode 54 with the optical emitter 204. In some implementations, the alignment mechanism 208 may include a keyed, pressure-fit connector. In other implementations, the alignment mechanism 208 may include a keyed, magnetic connector. In one example, the alignment mechanism 208 may include a magnet that is attracted to metal of the wearable computing device 10. In another example, the alignment mechanism 208 may include metal that is attracted to a magnet of the wearable computing device 10. The alignment mechanism 208 may employ any suitable mechanism to couple the communication cable 200 with the wearable computing device 10.

In some implementations, the alignment mechanism 208 may include optical barriers that separate the different communication channels. For example, the optical barriers may prevent communication light emitted by the optical emitter 52 from being detected by the photodiode 54. Likewise, the optical barriers may prevent communication light emitted by the optical emitter 204 from being detected by optical transducer 206.

A converter 210, which may be part of communication cable 200 or remote computing device 202, may be configured to encode communication data into an electrical signal that the optical emitter 204 translates into communication light emitted to the photodiode 54. Further, the converter 210 may be configured to extract communication data from an electrical signal produced by the optical transducer 206 responsive to receiving communication light from the optical emitter 52. The converter 210 may be configured to convert communication data of any suitable format to and/or from communication light.

In some implementations, the communication cable 200 may take a form of a wireless dongle configured to send communication data received optically from the wearable computing device 10 wirelessly to the remote computing device 202 via a wireless digital communication channel.

In some implementations, the communication cable 200 may take a form of an optical cable (e.g., a fiber-optic cable) that streams communication light (or optical data) received from the wearable computing device 10 to the remote computing device 202. In such implementations, the converter 210 may be omitted from the communication cable 200, and instead the converter may be incorporated into the remote computing device 202 in order to convert the optical data into a machine-understandable form of the optical data.

In some implementations, the wearable computing device 10 may include an inductive loop receiver 214 configured to receive an electrical charge from an inductive loop transmitter 216 of the communication cable 200. For example, the inductive electrical charge may be applied to re-charge energy-storage electronic components (e.g., a battery) of the wearable computing device 10. In some implementations, a magnetic connection created between the inductive loop receiver 214 and the inductive loop transmitter 216 may act as an alignment or coupling mechanism to couple the communication cable 200 to the wearable computing device 10.

By implementing optical communication and inductive charging componentry into the wearable computing device 10, any external electrical-connection interface may be omitted from the wearable computing device 10. Lacking any external electrical-connection interfaces, the wearable computing device 10 may be externally sealed (e.g., waterproofed). Moreover, in some implementations, the wearable computing device 10 may lack any external metal contacts pads.

Figure 3:
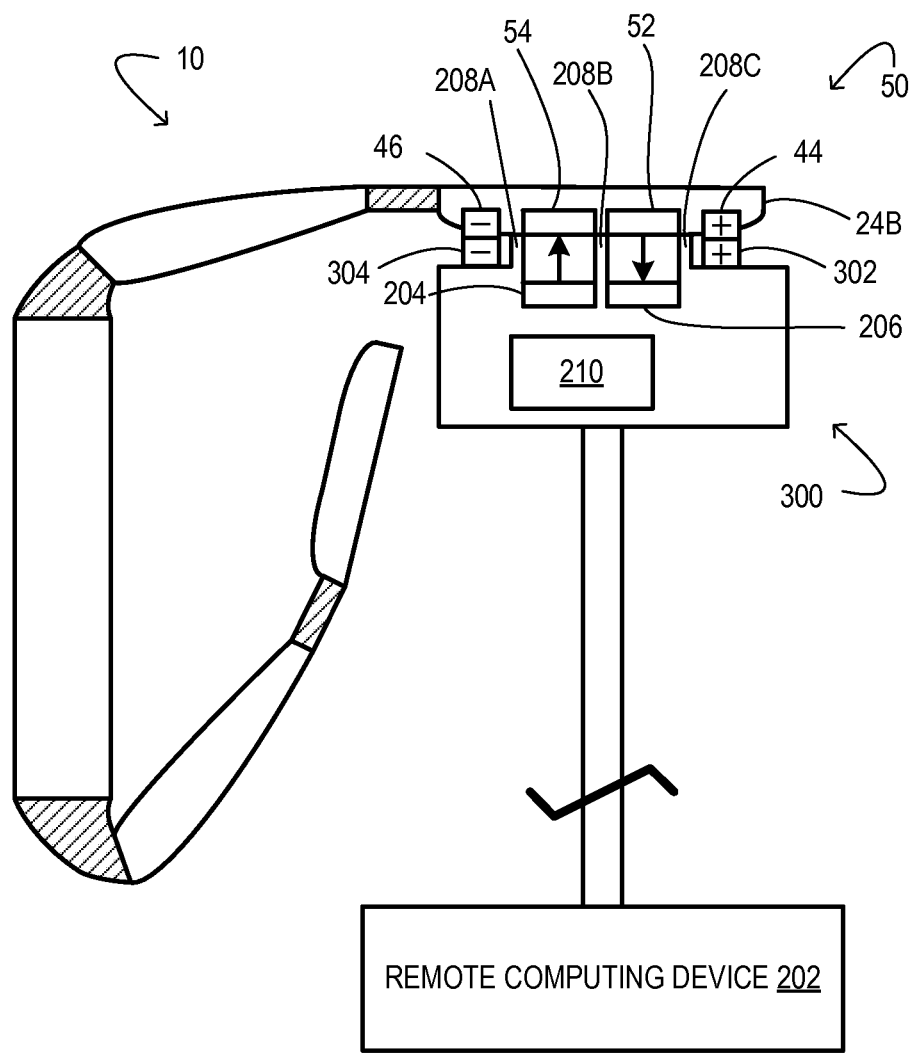
FIG. 3 shows another example implementation of a wearable computing device interfacing with a communication cable to enable optical communication with a remote computing device.

FIG. 3 shows another example implementation of the wearable computing device 10 interfacing with a communication cable 300 to enable optical communication with the remote computing device 202. Components of the communication cable 300 that may be substantially the same as those of the communication cable 200 are identified in the same way and are described no further. However, it will be noted that components identified in the same way in different implementations of the present disclosure may be at least partly different.

In the illustrated implementation, the wearable computing device 10 includes the pair of contact sensors—positive charging contact sensor or electrode 44 and negative contact sensor or electrode 46 arranged on pillow 24B of the band. Like, the electro-optical sensor 50, the pair of contact sensors 44 and 46 may play dual roles based on a mode of operation of the wearable computing device 10.

In one example, the wearable computing device 10 may be configured to, during the sensing/emitting mode, apply a diagnostic electrical signal across the positive electrode 44 and the negative electrode 46, and assess a galvanic skin response of the wearer of the wearable computing device 10 from the diagnostic electrical signal.

Furthermore, the communication cable 300 may include a positive Ohmic charging contact 302 and a negative Ohmic charging contact 304. The pair of Ohmic charging contacts 302 and 304 may be configured to interface with the pair of contact sensors 44 and 46 to create an electrical potential that allows the wearable computing device 10 to receive an electrical charge. For example, the electrical charge may be applied to re-charge energy-storage electronic components (e.g., a battery) of the wearable computing device 10.

In one example, the wearable computing device 10 may be configured to, during the communication mode, receive an electrical charge across the positive 44 electrode and the negative electrode 46 from the communication cable 300. In some implementations, the electrical charge may be applied while the communication cable 300 is mechanically aligned or coupled to the wearable computing device 10. Note that the positive electrode 44 and the negative electrode 46 may be positioned proximate to the electro-optical sensor 50 on the pillow 24B in order to limit an interface area between the communication cable 300 and the wearable computing device 10. Accordingly, a form factor of the communication cable 300 may be reduced.

In some implementations, the wearable computing device 10 may be configured to instruct the optical emitter 52 to provide communication light that is encoded with analog communication data indicative of electrical charging feedback. In one example, a light intensity of the communication light emitted by the optical emitter may be adjusted to indicate an amount of electrical charge desired to re-charge the wearable computing device 10.

Figure 4:
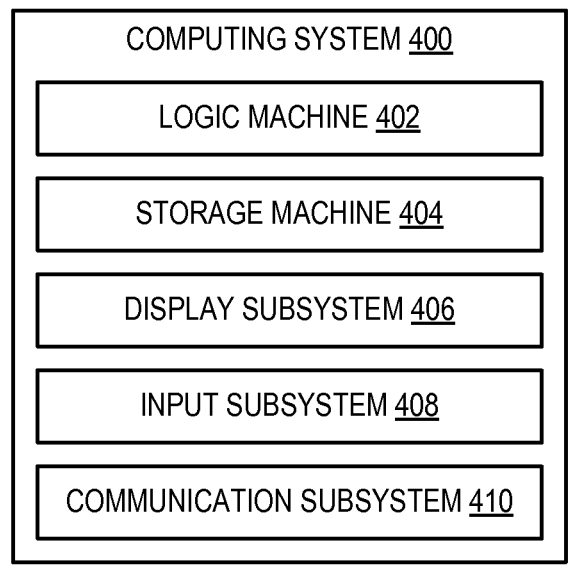
FIG. 4 shows an example computing system.

FIG. 4 schematically shows a non-limiting implementation of a computing system 400 that may be representative of a computing device of the present disclosure. For example, computing system 400 may be representative of wearable computing device 10 shown in FIGS. 1A, 1B, 2, and 3. Computing system 400 is shown in simplified form. Computing system 400 may take the form of one or more personal computers, server computers, tablet computers, home-entertainment computers, network computing devices, gaming devices, mobile computing devices, mobile communication devices (e.g., smart phone), and/or other computing devices.

Computing system 400 includes a logic machine 402 and a storage machine 404. Computing system 400 may optionally include a display subsystem 406, input subsystem 408, communication subsystem 410, and/or other components not shown in FIG. 4.

Logic machine 402 includes one or more physical devices configured to execute instructions. For example, the logic machine may be configured to execute instructions that are part of one or more applications, services, programs, routines, libraries, objects, components, data structures, or other logical constructs. Such instructions may be implemented to perform a task, implement a data type, transform the state of one or more components, achieve a technical effect, or otherwise arrive at a desired result.

The logic machine may include one or more processors configured to execute software instructions. Additionally or alternatively, the logic machine may include one or more hardware or firmware logic machines configured to execute hardware or firmware instructions. Processors of the logic machine may be single-core or multi-core, and the instructions executed thereon may be configured for sequential, parallel, and/or distributed processing. Individual components of the logic machine optionally may be distributed among two or more separate devices, which may be remotely located and/or configured for coordinated processing. Aspects of the logic machine may be virtualized and executed by remotely accessible, networked computing devices configured in a cloud-computing configuration.

Storage machine 404 may include removable and/or built-in devices. Storage machine 404 may include optical memory (e.g., CD, DVD, HD-DVD, Blu-Ray Disc, etc.), semiconductor memory (e.g., RAM, EPROM, EEPROM, etc.), and/or magnetic memory (e.g., hard-disk drive, floppy-disk drive, tape drive, MRAM, etc.), among others. Storage machine 404 may include volatile, nonvolatile, dynamic, static, read/write, read-only, random-access, sequential-access, location-addressable, file-addressable, and/or content-addressable devices.

It will be appreciated that storage machine 404 includes one or more physical devices. However, aspects of the instructions described herein alternatively may be propagated by a communication medium (e.g., an electromagnetic signal, an optical signal, etc.) that is not held by a physical device for a finite duration.

Aspects of logic machine 402 and storage machine 404 may be integrated together into one or more hardware-logic components. Such hardware-logic components may include field-programmable gate arrays (FPGAs), program- and application-specific integrated circuits (PASIC/ASICs), program- and application-specific standard products (PSSP/ASSPs), system-on-a-chip (SOC), and complex programmable logic devices (CPLDs), for example.

When included, display subsystem 406 may be used to present a visual representation of data held by storage machine 404. This visual representation may take the form of a graphical user interface (GUI). As the herein described operations and processes change the data held by the storage machine, and thus transform the state of the storage machine, the state of display subsystem 406 may likewise be transformed to visually represent changes in the underlying data. Display subsystem 406 may include one or more display devices utilizing virtually any type of technology. Such display devices may be combined with logic machine 402 and/or storage machine 404 in a shared enclosure, or such display devices may be peripheral display devices.

When included, input subsystem 408 may comprise or interface with one or more user-input devices such as a keyboard, mouse, touch screen, or game controller. In some implementations, the input subsystem may comprise or interface with selected natural user input (NUI) componentry. Such componentry may be integrated or peripheral, and the transduction and/or processing of input actions may be handled on- or off-board. Example NUI componentry may include a microphone for speech and/or voice recognition; an infrared, color, stereoscopic, and/or depth camera for machine vision and/or gesture recognition; a head tracker, eye tracker, accelerometer, and/or gyroscope for motion detection and/or intent recognition; as well as electric-field sensing componentry for assessing brain activity.

When included, communication subsystem 410 may be configured to communicatively couple computing system 400 with one or more other computing devices. Communication subsystem 410 may include wired and/or wireless communication devices compatible with one or more different communication protocols. As non-limiting examples, the communication subsystem may be configured for communication via a wireless telephone network, or a wired or wireless local- or wide-area network. In some implementations, the communication subsystem may allow computing system 400 to send and/or receive messages to and/or from other devices via a network such as the Internet.

Another example provides a wearable computing device including an electro-optical sensor to translate received light into an electrical signal, a logic machine, and a storage machine holding instructions executable by the logic machine to during a first mode, assess a physical parameter of a wearer of the wearable computing device from the electrical signal, and during a second mode, extract communication data encoded in the electrical signal. In such an example, optionally the electro-optical sensor is a pulse oximeter, and the physical parameter is a blood oxygen level. In such an example, optionally the electro-optical sensor is an optical pulse rate sensor, and the physical parameter is a pulse rate of the wearer. In such an example, the wearable computing device optionally includes an optical emitter to emit a diagnostic reference light. The electro-optical sensor is configured to translate the diagnostic reference light and a communication light into an electrical signal, and the storage machine holds instructions executable by the logic machine to during the first mode, instruct the optical emitter to emit the diagnostic reference light, during the first mode, recognize the electrical signal translated from the diagnostic reference light, during the second mode, allow the optical emitter to not emit the diagnostic reference light, and during the second mode, recognize the electrical signal translated from the communication light. In such an example, optionally the optical emitter is a light emitting diode. In such an example, optionally the storage machine holds instructions executable by the logic machine to, during the second mode, instruct the optical emitter to emit communication light encoding communication data. In such an example, optionally during the second mode, the received light is received from a communication cable. In such an example, optionally the wearable computing device includes an alignment mechanism to align the electro-optical sensor with an optical emitter of the communication cable and align the optical emitter with an electro-optical sensor of the communication cable. In such an example, optionally the wearable computing device includes an inductive loop receiver to receive an electrical charge from an inductive loop transmitter of the communication cable. In such an example, optionally the wearable computing device includes a band to couple the wearable computing device to the wearer, a skin conductance sensor including a first electrode positioned in a first portion of the band to contact a first portion of skin of the wearer and a second electrode positioned in a second portion of the band to contact a second portion of skin of the wearer; and wherein the storage machine holds instructions executable by the logic machine to during the first mode, apply a diagnostic electrical signal across the first electrode and the second electrode, during the first mode, assess a galvanic skin response of the wearer of the wearable computing device from the diagnostic electrical signal, and during the second mode, receive an electrical charge across the first electrode and the second electrode from the communication cable. Any or all of the above-described examples may be combined in any suitable manner in various implementations.

Another example provides a wearable computing device including an optical emitter to emit a diagnostic reference light, an electro-optical sensor to translate diagnostic reference light and communication light into an electrical signal, a logic machine, and a storage machine holding instructions executable by the logic machine to during a first mode, instruct the optical emitter to emit the diagnostic reference light, during the first mode, recognize the electrical signal translated from the diagnostic reference light, during the first mode, assess a physical parameter of a wearer of the wearable computing device from the electrical signal, during a second mode, allow the optical emitter to not emit the diagnostic reference light, during the second mode, recognize the electrical signal translated from the communication light, and during the second mode, extract communication data encoded in the electrical signal. In such an example, optionally the electro-optical sensor is a pulse oximeter, and the physical parameter is a blood oxygen level. In such an example, optionally the electro-optical sensor is an optical pulse rate sensor, and the physical parameter is a pulse rate of the wearer. In such an example, optionally the optical emitter is a light emitting diode. In such an example, optionally the storage machine holds instructions executable by the logic machine to, during the second mode, instruct the optical emitter to emit communication light encoding communication data. In such an example, optionally during the second mode, the received light is received from a communication cable. In such an example, optionally the wearable computing device includes an alignment mechanism to align the electro-optical sensor with an optical emitter of the communication cable and align the optical emitter with an electro-optical sensor of the communication cable. In such an example, optionally the wearable computing device includes an inductive loop receiver to receive an electrical charge from an inductive loop transmitter of the communication cable. In such an example, optionally the wearable computing device includes a band to couple the wearable computing device to the wearer, a skin conductance sensor including a first electrode positioned in a first portion of the band to contact a first portion of skin of the wearer and a second electrode positioned in a second portion of the band to contact a second portion of skin of the wearer, and the storage machine holds instructions executable by the logic machine to during the first mode, apply a diagnostic electrical signal across the first electrode and the second electrode, during the first mode, assess a galvanic skin response of the wearer of the wearable computing device from the diagnostic electrical signal, and during the second mode, receive an electrical charge across the first electrode and the second electrode from the communication cable. Any or all of the above-described examples may be combined in any suitable manner in various implementations.

Another example provides a computing device including an electro-optical sensor to translate received light into an electrical signal, a logic machine, and a storage machine holding instructions executable by the logic machine to during a first mode, assess a physical parameter of an environment of the computing device from the electrical signal, and during a second mode, extract communication data encoded in the electrical signal.

It will be understood that the configurations and/or approaches described herein are exemplary in nature, and that these specific implementations or examples are not to be considered in a limiting sense, because numerous variations are possible. The specific routines or operations described herein may represent one or more of any number of processing strategies. As such, various acts illustrated and/or described may be performed in the sequence illustrated and/or described, in other sequences, in parallel, or omitted. Likewise, the order of the above-described processes may be changed.

The subject matter of the present disclosure includes all novel and nonobvious combinations and subcombinations of the various processes, systems and configurations, and other features, functions, acts, and/or properties disclosed herein, as well as any and all equivalents thereof.

The invention claimed is:

1. A wearable computing device comprising:
   a band configured to couple the wearable computing device to a wrist of a wearer;
   an electro-optical sensor arranged on the band to face the wrist and configured to translate received light into an electrical signal;
   an alignment mechanism configured to align the electro-optical sensor with an optical emitter of a communication cable, wherein the wearable computing device is configured to sense connection of the communication cable;
   a logic machine; and
   a storage machine holding instructions executable by the logic machine to:
      during a first mode, assess a physical parameter of the wearer of the wearable computing device from the electrical signal; and
      during a second mode, extract communication data encoded in the electrical signal that is translated, via the electro-optical sensor, from light received from the optical emitter of the communication cable, and wherein the wearable computing device is configured to automatically switch from the first mode to the second mode based on sensing connection of the communication cable to the wearable computing device.

2. The wearable computing device of claim 1, wherein the electro-optical sensor is a pulse oximeter, and the physical parameter is a blood oxygen level.

3. The wearable computing device of claim 1, wherein the electro-optical sensor is an optical pulse rate sensor, and the physical parameter is a pulse rate of the wearer.

4. The wearable computing device of claim 1, further comprising:
an optical emitter to emit a diagnostic reference light;
wherein the electro-optical sensor is configured to translate the diagnostic reference light and a communication light emitted by the optical emitter of the communication cable into the electrical signal; and
wherein the storage machine further holds instructions executable by the logic machine to:
during the first mode, instruct the optical emitter of the wearable computing device to emit the diagnostic reference light;
during the first mode, recognize the electrical signal translated from the diagnostic reference light; and
during the second mode, recognize the electrical signal translated from the communication light.

5. The wearable computing device of claim 4, wherein the optical emitter of the wearable computing device is a light emitting diode.

6. The wearable computing device of claim 4, wherein the storage machine further holds instructions executable by the logic machine to, during the second mode, instruct the optical emitter to emit communication light encoding communication data.

7. The wearable computing device of claim 4,
wherein the alignment mechanism is configured to align the optical emitter of the wearable computing device with an electro-optical sensor of the communication cable.

8. The wearable computing device of claim 1, further comprising:
an inductive loop receiver to receive an electrical charge from an inductive loop transmitter of the communication cable.

9. The wearable computing device of claim 1, further comprises:
a skin conductance sensor including a first electrode positioned in a first portion of the band to contact a first portion of skin of the wearer and a second electrode positioned in a second portion of the band to contact a second portion of skin of the wearer; and wherein the storage machine further holds instructions executable by the logic machine to:
during the first mode, apply a diagnostic electrical signal across the first electrode and the second electrode;
during the first mode, assess a galvanic skin response of the wearer of the wearable computing device from the diagnostic electrical signal; and
during the second mode, receive an electrical charge across the first electrode and the second electrode from the communication cable.

10. The wearable computing device of claim 9, wherein the storage machine further holds instructions executable by the logic machine to:

automatically switch from the first mode to the second mode based on the galvanic skin response indicating that the wearable computing device is not being worn by the wearer; and
automatically switch from the second mode to the first mode based on the first electrode and the second electrode subsequently not receiving the electrical charge from the communication cable.

11. The wearable computing device of claim 1, further comprising:
a wireless communication interface configured to wirelessly communicate with a remote computing device; and
wherein the storage machine further holds instructions executable by the logic machine to:
during the first mode, wirelessly communicate with the remote computing device via the wireless communication interface; and
automatically switch to operation in the second mode to receive, via the electro-optical sensor, the communication data without wirelessly communicating with the remote computing device based on detecting installation of a corrupted version of firmware on the wearable computing device.

12. A wearable computing device comprising:
a band configured to couple the wearable computing device to a wrist of a wearer;
an optical emitter arranged on the band to face the wrist and configured to emit a diagnostic reference light;
an electro-optical sensor arranged on the band to face the wrist and configured to translate the diagnostic reference light and a communication light emitted from an optical emitter of a communication cable into an electrical signal;
an alignment mechanism configured to align the electro-optical sensor with the optical emitter of the communication cable, wherein the wearable computing device is configured to sense connection of the communication cable;
a logic machine; and
a storage machine holding instructions executable by the logic machine to:
during a first mode, instruct the optical emitter of the wearable computing device to emit the diagnostic reference light;
during the first mode, recognize, via the electro-optical sensor, the electrical signal translated from the diagnostic reference light;
during the first mode, assess a physical parameter of the wearer of the wearable computing device from the recognized electrical signal;
during a second mode, recognize, via the electro-optical sensor, the electrical signal translated from the communication light emitted from the optical emitter of the communication cable, and
during the second mode, extract communication data encoded in the recognized electrical signal, and wherein the wearable computing device is configured to automatically switch from the first mode to the second mode based on sensing connection of the communication cable to the wearable computing device.

13. The wearable computing device of claim 12, wherein the electro-optical sensor is a pulse oximeter, and the physical parameter is a blood oxygen level.

14. The wearable computing device of claim 12, wherein the electro-optical sensor is an optical pulse rate sensor, and the physical parameter is a pulse rate of the wearer.

15. The wearable computing device of claim 12, wherein the optical emitter of the wearable computing device is a light emitting diode.

16. The wearable computing device of claim 12, wherein the storage machine further holds instructions executable by the logic machine to, during the second mode, instruct the optical emitter of the wearable computing device to emit communication light encoding communication data to an electro-optical sensor of the communication cable.

17. The wearable computing device of claim 12,
wherein the alignment mechanism is configured to align the optical emitter of the wearable computing device with an electro-optical sensor of the communication cable.

18. The wearable computing device of claim 12, further comprising:
an inductive loop receiver to receive an electrical charge from an inductive loop transmitter of the communication cable.

19. The wearable computing device of claim 12, further comprises:
a skin conductance sensor including a first electrode positioned in a first portion of the band to contact a first portion of skin of the wearer and a second electrode positioned in a second portion of the band to contact a second portion of skin of the wearer; and
wherein the storage machine further holds instructions executable by the logic machine to:
during the first mode, apply a diagnostic electrical signal across the first electrode and the second electrode;
during the first mode, assess a galvanic skin response of the wearer of the wearable computing device from the diagnostic electrical signal; and
during the second mode, receive an electrical charge across the first electrode and the second electrode from the communication cable.

20. A wearable computing device comprising:
a band configured to couple the wearable computing device to a wrist of a wearer;
an optical emitter arranged on the band to face the wrist and configured to emit a diagnostic reference light or a communication light;
an electro-optical sensor to translate received light into an electrical signal;
an alignment mechanism configured to align the optical emitter of the wearable computing device with an electro-optical sensor of a communication cable, and align the electro-optical sensor of the wearable computing device with an optical emitter of the communication cable, and wherein the wearable computing device is configured to sense connection of the communication cable;
a logic machine; and
a storage machine holding instructions executable by the logic machine to:
during a first mode, instruct the optical emitter of the wearable computing device to emit the diagnostic reference light;
during the first mode, assess a physical parameter of the wearer from the electrical signal translated from the diagnostic reference light via the electro-optical sensor of the wearable computing device;
during a second mode, extract communication data encoded in the electrical signal that is translated, via the electro-optical sensor, from communication light received from the optical emitter of the communication cable; and
during the second mode, instruct the optical emitter of the wearable computing device to emit communication light to the electro-optical sensor of the communication cable, and wherein the wearable computing device is configured to automatically switch from the first mode to the second mode based on sensing connection of the communication cable to the wearable computing device.

* * * * *